(12) United States Patent
Le Guay et al.

(10) Patent No.: US 8,062,035 B2
(45) Date of Patent: Nov. 22, 2011

(54) EXTRACTIBLE ANCHORING POST MADE FROM COMPOSITE MATERIAL

(75) Inventors: Yannick Le Guay, Renage (FR); Bruno Clunet-Coste, Saint Etienne de Crossey (FR)

(73) Assignees: Bernard Mancuf, Voiron (FR); Bruno Clunet-Coste, Saint Etienne de Crossey (FR); Andre Collombin, Voiron (FR)

( * ) Notice: Subject to any disclaimer, the term of this patent is extended or adjusted under 35 U.S.C. 154(b) by 541 days.

(21) Appl. No.: 12/216,166

(22) Filed: Jun. 30, 2008

(65) Prior Publication Data
US 2009/0325130 A1 Dec. 31, 2009

(51) Int. Cl.
*A61C 5/02* (2006.01)
(52) U.S. Cl. .......................................... 433/224; 433/81
(58) Field of Classification Search ................... 433/212, 433/201.1, 220, 221, 222.1, 225; 428/296.7
See application file for complete search history.

(56) References Cited

U.S. PATENT DOCUMENTS

| | | | |
|---|---|---|---|
| 5,871,359 A | 2/1999 | Billet et al. | |
| 5,890,904 A | 4/1999 | Reynaud et al. | |
| 6,012,924 A * | 1/2000 | Reynaud et al. | 433/220 |
| 6,183,253 B1 | 2/2001 | Billet et al. | |
| 6,827,576 B2 * | 12/2004 | Karmaker et al. | 433/220 |
| 7,235,290 B2 * | 6/2007 | Vallittu et al. | 428/296.7 |
| 2001/0026913 A1 * | 10/2001 | Xu et al. | 433/228.1 |
| 2004/0241609 A1 * | 12/2004 | Jia et al. | 433/167 |
| 2005/0123881 A1 | 6/2005 | Karmaker et al. | |

FOREIGN PATENT DOCUMENTS

| | | |
|---|---|---|
| EP | 1 147 748 A2 | 10/2001 |
| EP | 1 806 110 A1 | 1/2006 |
| FR | 2 626 167 A1 | 7/1989 |
| FR | 2 588 181 B1 | 4/1990 |
| FR | 2 726 999 B1 | 1/1997 |
| FR | 2 731 147 B1 | 5/1997 |
| FR | 2 753 365 A1 | 3/1998 |
| FR | 2 861 287 A1 | 4/2005 |
| FR | 2 895 666 | 7/2007 |

* cited by examiner

*Primary Examiner* — Cris L Rodriguez
*Assistant Examiner* — Matthew Saunders
(74) *Attorney, Agent, or Firm* — Oliff & Berridge, PLC

(57) ABSTRACT

A canal anchoring post formed by a single composite material comprising at least an organic matrix, particles and fibers. The particles and fibers are distributed in the organic matrix with respective volume proportions varying progressively and radially from the central longitudinal axis to the periphery of said post. In addition, the respective variations of the volume proportions of particles and fibers are opposite and the sum of the volume proportions of particles and fibers is radially constant from the central longitudinal axis to the periphery of said post.

10 Claims, 3 Drawing Sheets

EXTRACTIBLE ANCHORING POST MADE FROM COMPOSITE MATERIAL

BACKGROUND OF THE INVENTION

The invention relates to a canal anchoring post more particularly designed to secure coronal fillings respecting the anatomical and physiological particularities of the root canal.

STATE OF THE ART

With reference to FIG. 1 relative to reconstruction of a coronal part of the tooth, a post 1 is generally inserted and sealed in the root canal 2 after shaping to act as foundation for coronal reconstitution. The posts can be made from metallic material or from composite material.

Composite material posts are made up of an organic matrix 3 binding together fibers 4 that give the post its mechanical resilience features, and possibly of organic or mineral particles 5 providing other features, for example a specific shade of coloring, opacity to X-rays, or translucence to enable polymerization of photosensitive sealants.

The document FR 2 588 181 precisely describes the possibility of securing posts by means of photosensitive sealants, which implies translucence of such posts.

In case of an apical infection or a prosthetic defect requiring removal of a composite material post, the dental surgeon has to eliminate the existing post solidly secured in the root by grinding or drilling with a large risk of creating a false canal 6.

A method consisting in inserting a drill bit 7 rotating at 15,000 rpm in the post without irrigation has also been proposed. Nothing happens for a few seconds, then the organic matrix heats and deforms by buckling. It has been observed that the fibers do not enable precise guiding of the drill, and the risk of perforation remains very great, as indicated schematically in FIG. 1.

The document FR 2 588 181 describes a post having a hollow central core.

The document FR 2 626 167 refers to a post having a central core that is metallic or is formed by fibers coated with synthetic resin.

When this core is not metallic, it is formed by a fiber or by several non-radiopaque fibers, and the outer sheath can be made opaque to X-rays by means of radiopaque particles.

The document FR 2 731 147 mentions a post equipped with a central core made from composite material that comprises at least one mesh of non-radiopaque fibers and a radiopaque external sheath reinforced with fibers opaque to X-rays.

The document FR 2 726 999 describes a post having a central core that is easy to penetrate and transparent to act as light guide, but being made from a different material from the rest of the post.

The document U.S. Pat. No. 5,326,263 relates to a tool entirely made of translucent plastic material enabling photosensitive resins to be polymerized in depth in the dental canal. This tool can advantageously be equipped with a removable central optic fiber.

In the document US-A-2005/123881, a post according to a particular embodiment comprises a cylindrical-shaped central part made of composite material reinforced by fibers and an annular peripheral part coaxial to the central part and made of composite material reinforced by fibers and/or charges. One of the two parts is radiopaque whereas the other part is transparent or translucent. The central part can thus be radiopaque whereas the peripheral part is transparent or translucent.

Incorporating a central core made from chemically and mechanically different material in the post creates a fragile zone between materials of different natures at the level of the interface where the mechanical stresses are concentrated. This results in the appearance of interfacial tensions and beginnings of breaks on account of the incompatibility of the materials in presence, with a risk of infiltration along the interface. Moreover, centering such a core in the center of a post is random and difficult to reproduce industrially.

OBJECT OF THE INVENTION

The object of the invention is to provide a canal anchoring post made of composite material comprising at least one organic matrix, particles and fibers that does not present the shortcomings described above.

According to the invention, this object is achieved by the appended claims.

BRIEF DESCRIPTION OF THE DRAWINGS

Other advantages and features will become more clearly apparent from the following description of particular embodiments of the invention given as non-restrictive examples only and represented in the accompanying drawings, in which.

DESCRIPTION OF PARTICULAR EMBODIMENTS

Figure 1:
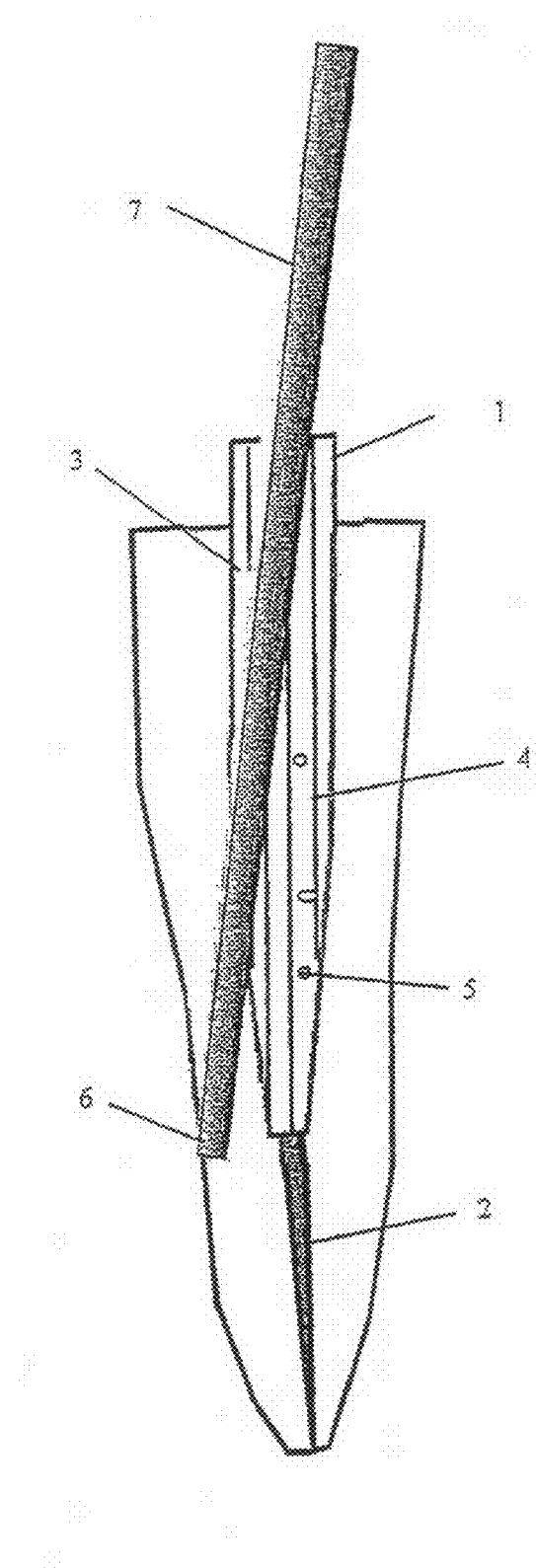
FIG. 1 is a schematic view of a prior reconstruction phase of the coronal part of a tooth, before extraction of an existing post of the prior art.

A canal anchoring post according to the invention is formed by a single composite material comprising at least one organic matrix, particles and strengthening fibers.

Moreover, the volume distribution of the particles and that of the strengthening fibers in the organic matrix of the post vary from the center of the post to the periphery of the post.

In particular, the particles and fibers are arranged in an organic matrix with respective volume proportions varying progressively and radially from a central longitudinal axis of said post to the periphery of said post. The respective variations of the volume proportions of the particles and fibers are in fact opposite. The sum of the volume proportions in particles and fibers is moreover radially constant from the central longitudinal axis to the periphery of said post.

Advantageously, the evolution of the volume proportion of fibers is increasing from the longitudinal axis to the periphery of the post whereas, for the particles, the evolution of their volume proportion is decreasing.

What is meant by volume proportion of particles is the ratio between the volume occupied by the particles and the total volume occupied by the particles and fibers. Likewise, the volume proportion of fibers corresponds to the ratio between the volume occupied by the fibers and the total volume occupied by the particles and fibers. The term volume proportion can also be replaced by the term volume ratio or volume percentage.

According to a particular embodiment, the majority of the particles can be formed by radiopaque particles. Said radiopaque particles are for example chosen from any type of charge containing a metal such as heavy metals or rare earths, more particularly in oxide or fluoride form. More particularly, the radiopaque particles can be chosen from the oxides or fluorides of a chemical element having an atomic number comprised between 57 and 71, such as ytterbium oxide ($Yb_2O_3$) ytterbium fluoride ($YbF_3$), gadolinium oxide ($Gd_2O_3$) and dysprosium oxide. They can also be chosen from barium oxide ($Ba_2O_3$), tantalum oxide ($Ta_2O_5$), zirconium oxide ($ZrO_2$), yttrium oxide ($Y_2O_3$) or from particles of glasses containing opacifying elements, such as lanthanum, zirconium, tantalum, strontium, tungsten or niobium glass.

The composite material forming the post can moreover also comprise non-radiopaque particles, in particular when other properties are sought for, for example for esthetic reasons, codification reasons or on account of manufacturing requirements. The non-radiopaque particles are for example chosen from mineral or organo-mineral particles not containing any heavy elements, for example glass beads or ballotini, silica beads, colloidal or pyrogenated silica, talc, calcium carbonate ($CaCO_3$), alumina ($Al_2O_3$) and titanium oxide ($TiO_2$).

The composite material can also comprise colored particles. It can for example contain particles of organic colorants or thermochromatic colorants, such as thermochromatic liquid crystals, leuco-colorant (also known as leuco dye) thermochromatic microcapsules, spirolactones, fluorans, spiropyranes or fulgides, in combination or not with conventional pigments or colorants such as titanium oxide, iron oxide, ultramarine and various organic pigments.

The reinforcing fibers are preferably fibers enhancing the mechanical properties and in particular the flexural, tensile, compressive and shear strength and also the hardness of the composite material. Among the numerous reinforcing fibers available, glass fiber can be chosen for its good mechanical properties and its ability to conduct light. Furthermore, the post can comprise at least two types of reinforcing fibers. The fibers can also be at least partially formed by other vitreous mineral fibers and/or by other manufactured organic fibers such as fibers with a polyamide, polyester, acrylic, polypropylene or aramide base.

Any type of resin suitable for the dental material field can be used, among which a methacrylate resin of dimethacrylate urethane type known for its good biocompatibility should for example be chosen. Other types of resin can also be used, in particular polymethacrylate-base resins, bisphenol A glycol dimethacrylate, triethylene glycol methacrylate, polyester, epoxy and modified epoxy resins.

Figure 2:
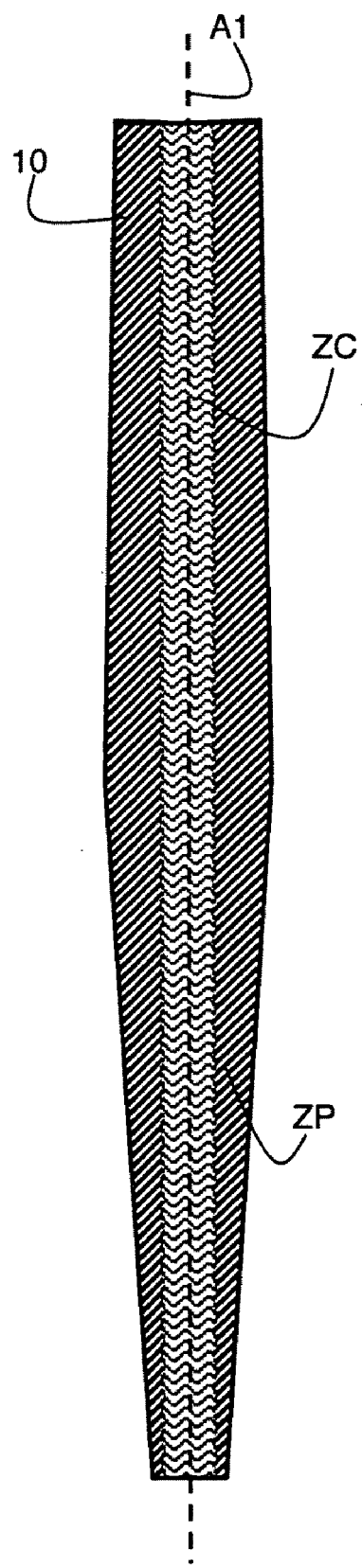
FIG. 2 represents a particular embodiment of an extractible prefabricated post.

A central zone ZC along the central longitudinal axis A1 of post 10 and an annular peripheral zone ZP, coaxial to said central zone ZC, can be delineated by a particular modification of the distribution of the fibers and particles in the post, as represented in FIG. 2.

In particular, the limit between central zone ZC and peripheral zone ZP can be defined by the fact that, in central zone ZC, the volume proportion of particles is greater than the volume proportion of fibers, whereas in the peripheral zone ZP the volume proportion of particles is smaller than the volume proportion of fibers.

The two zones ZC and ZP of post 10 are thereby constituted by the same organic matrix. The two zones therefore do not need to be manufactured separately before being assembled. They can be produced in a single operation, for example by pultrusion. The post is then chemically homogeneous and does not have any chemical interfaces, which eliminates any interfacial tension and beginning of breaking, and also any risk of infiltration.

For example, the particles present in post 10 can be of two types: radiopaque particles and non-radiopaque particles. Furthermore, central zone ZC of post 10 can comprise the radiopaque particles, such as for example $YbF_3$ particles, whereas peripheral zone ZP can comprise non-radiopaque particles, for example nanometric silica particles. In this case, the central zone is radiopaque whereas the peripheral zone is not radiopaque.

According to an alternative embodiment, the respective volume proportions of radiopaque and non-radiopaque particles can be modified progressively and radially from longitudinal axis A1 up to the periphery of said post 10, with opposite respective variations. Thus, in this case, the variations of the volume proportions of radiopaque and non-radiopaque particles are preferably respectively decreasing and increasing from the longitudinal axis to the periphery of the post. In this case, central zone ZC presents a higher radiopaqueness than that of peripheral zone ZP.

Furthermore, when the volume proportion of fibers in peripheral zone ZP is greater than the volume proportion of fibers in central zone ZC, peripheral zone ZP presents a greater hardness than that of central zone ZC. This hardness differential does however constitute a drilling guide centered along longitudinal axis A1 of the post and enables safety guiding in case removal is necessary.

Furthermore, the strengthening fibers can be of two types in post 10. In particular, peripheral zone ZP of post 10 can for example contain glass fibers of E type, whereas central zone ZC of said post 10 can contain glass fibers of different composition, for example fibers noted AR, R, or S2 type, ECR glass from Advantex, silica (quartz), alumina, $ZrO_2$, or boron fibers.

A post according to the invention presents the advantage of being able to be implemented by means of a single pultrusion operation. This guarantees a controlled radial distribution of the reinforcements. The non equally drawn unitary filaments are statistically mixed with one another on input to the die to keep the diameter of central zone ZC constant throughout the pultrusion process.

Figure 3:
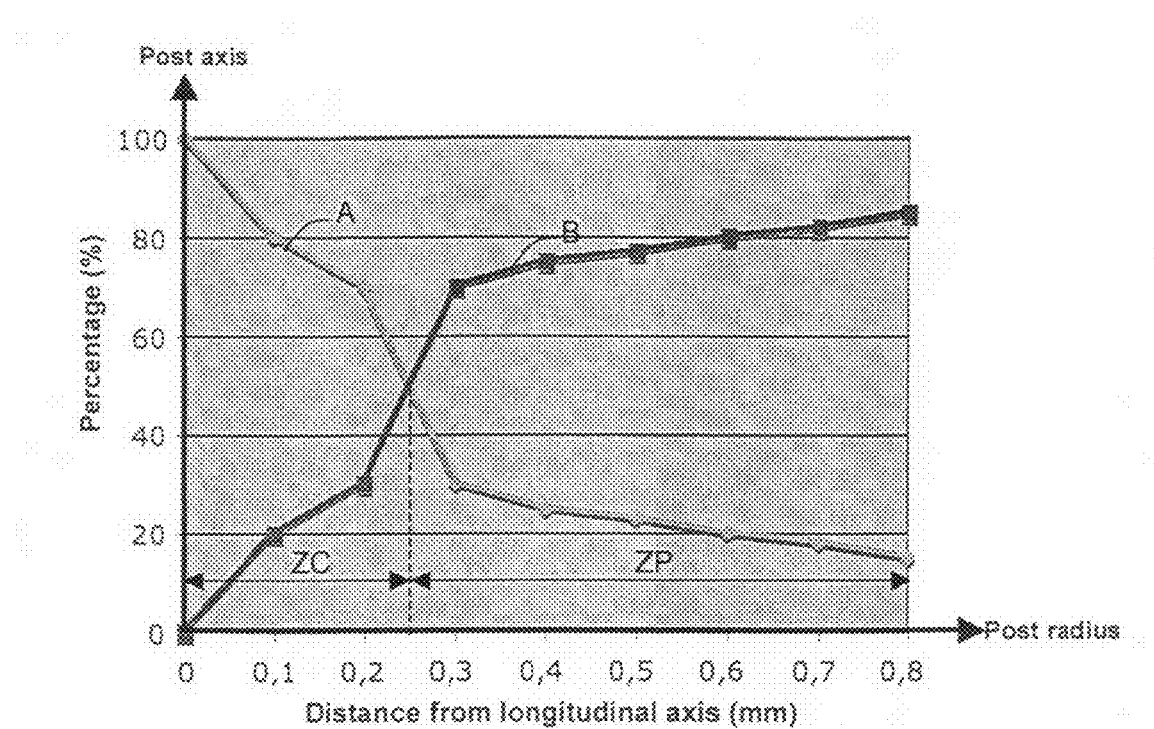
FIG. 3 represents a particular evolution of the respective volume proportions of the particles and fibers in a post.

For example purposes, FIG. 3 represents a particular evolution of the respective total volume proportions of the particles (plot A) and reinforcing fibers (plot B) in a particular embodiment of a post 10 according to the invention, from longitudinal axis A1 of said post 10 to the periphery thereof. At the level of its central longitudinal axis A1, post 10 comprises 100% of particles in volume, whereas at its periphery it comprises 85% of fibers and 15% of particles in volume. Between longitudinal axis A1 and the periphery, the total volume proportion of particles decreases gradually whereas the total volume proportion of fibers increases gradually. In such a post, the abscissa of point I, which corresponds to the intersection between curves A and B, defines an interface between central zone ZC and peripheral zone ZP. Before this intersection I, the volume proportion of particles is in fact higher than the volume proportion of fibers, and after this intersection I, the volume proportion of particles is lower than the volume proportion of fibers. This interface does not however constitute a physical interface liable to create inhomogeneities in the post, as the organic matrix is common to the whole of the post and the volume proportions of fibers and particles vary progressively. Such a post is in particular manufactured by a single operation, for example a pultrusion operation.

Figure 4:
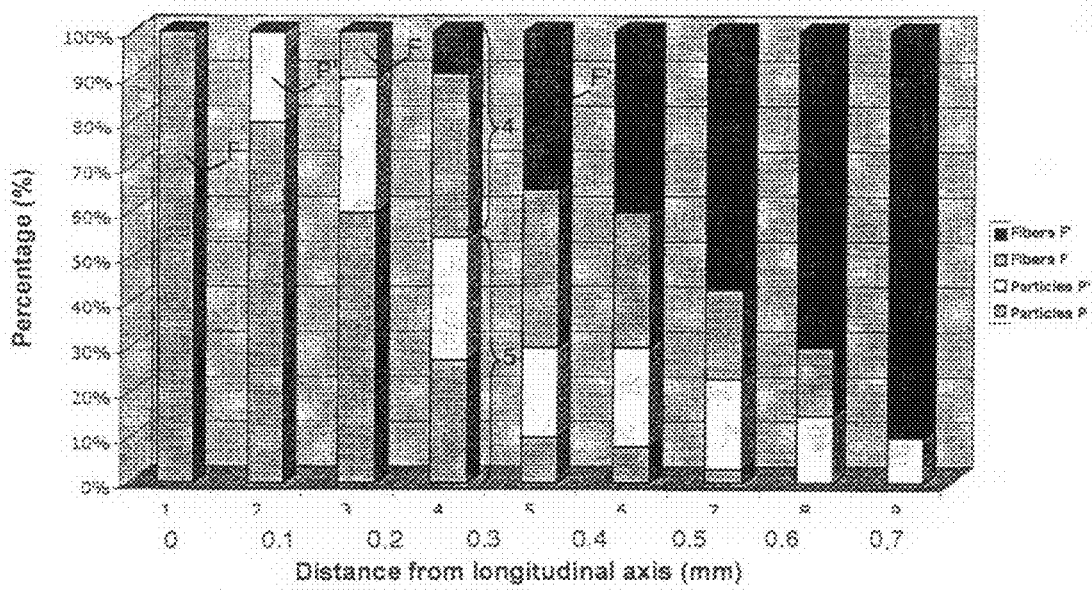
FIG. 4 represents another distribution of two types of particles and two types of fibers in an organic matrix of a post.

FIG. 4 represents a particular embodiment of the distribution of two types of particles P and P' and of two types of fibers F and F' in an organic matrix of a post 10 according to the invention, from longitudinal axis A1 of said post 10 to the periphery thereof.

In this particular case, the post comprises 100% in volume of particles P at the level of its longitudinal axis A1, the proportion of particles P decreasing progressively as we move away from the longitudinal axis to drop to zero about 0.7 mm from the axis, to the benefit of particles P' and fibers F and F'. Furthermore, near the longitudinal axis of the post and more precisely in a central zone ZC of the post, the total volume proportion of particles P and P' is larger than the total proportion of fibers F and F' and vice-versa at the periphery and more particularly in a peripheral zone ZP of the post. Finally, the volume proportion of fibers F' increases progressively from the longitudinal axis to the periphery of the post. Such a radial distribution of the particles and fibers can be obtained by pultrusion.

The post according to the invention can be of any shape, for example cylindrical, conical or cylindro-conical, and in the latter cases presents a decreasing elasticity modulus from the coronal part to the apex.

We claim:

1. A canal anchoring post consisting of a composite material comprising:
   a single cured organic matrix,
   particles, and
   fibers, wherein:
      the particles are distributed inside the single cured organic matrix according to a volume proportion of particles, corresponding to a ratio between the volume occupied by the particles inside the single cured organic matrix and the total volume occupied by the particles and by the fibers inside the single cured organic matrix and varying progressively and radially inside the single cured organic matrix from a central longitudinal axis of said post to the periphery of said post,
      the fibers are distributed inside the single cured organic matrix according to a volume proportion of fibers, corresponding to a ratio between the volume occupied by the fibers inside the single cured organic matrix and the total volume occupied by the particles and by the fibers inside the single cured organic matrix and varying progressively and radially inside the single cured organic matrix from a central longitudinal axis of said post to the periphery of said post,
      the variation of the volume proportion of particles and the variation of the volume proportion of fibers are opposite, and
      the sum of the volume proportion of particles and the volume proportion of fibers is radially constant from the central longitudinal axis to the periphery of said post.

2. The post according to claim 1, wherein the composite material contains at least two types of particles.

3. The post according to claim 2, wherein the two types of particles are respectively radiopaque and non-radiopaque.

4. The post according to claim 3, wherein the radiopaque particles and the non-radiopaque particles are respectively distributed in the organic matrix with volume proportions varying progressively and radially from the central longitudinal axis to the periphery of said post and wherein the respective variations of the volume proportions of radiopaque particles and of non-radiopaque particles are opposite.

5. The post according to claim 1, wherein the composite material comprises at least two types of fibers.

6. The post according to claim 5, wherein the two types of fibers are respectively distributed in the organic matrix with volume proportions varying progressively and radially from the central longitudinal axis to the periphery of said post and wherein the respective variations of the volume proportions of the two types of fibers are opposite.

7. The post according to claim 1, wherein the fibers and particles are distributed in the organic matrix in a single pultrusion operation.

8. The post according to claim 1, wherein the evolution of the volume proportion of fibers is increasing from the longitudinal axis to the periphery of the post and the evolution of the volume proportion of the particles is decreasing from the longitudinal axis to the periphery of the post.

9. The post according to claim 8, wherein the volume proportion of particles is greater than the volume proportion of the fibers in a central zone along the central longitudinal axis of the post, and the volume proportion of particles is smaller than the volume proportion of the fibers in a peripheral zone coaxial to the central longitudinal axis of the post.

10. The post according to claim 9, wherein a peripheral zone of the canal anchoring post has a greater hardness than a central zone of the canal anchoring post.

* * * * *